United States Patent [19]

Chakupurakal

[11] 4,327,122
[45] Apr. 27, 1982

[54] EVAPORATED ELECTRODES FOR ZIRCONIA EXHAUST GAS OXYGEN SENSORS

[75] Inventor: Thomas Chakupurakal, St. Clair Shores, Mich.

[73] Assignee: General Motors Corporation, Detroit, Mich.

[21] Appl. No.: 177,617

[22] Filed: Aug. 13, 1980

[51] Int. Cl.³ .............................................. B05D 5/12
[52] U.S. Cl. ..................................... 427/57; 427/105; 427/124; 427/125; 427/237; 427/238; 427/250; 427/255; 427/309; 427/314; 204/195 S; 118/724; 118/726; 156/637; 156/667
[58] Field of Search ................ 118/726, 724; 427/105, 427/124, 125, 237, 238, 250, 255, 309, 314, 57; 204/195 S; 134/1; 156/637, 667

[56] References Cited

U.S. PATENT DOCUMENTS

| | | | |
|---|---|---|---|
| 1,738,991 | 12/1929 | Fink et al. ............................ | 118/726 |
| 3,296,012 | 1/1967 | Stalnecker ........................... | 427/309 |
| 3,431,615 | 3/1969 | Hagadorn et al. ................. | 29/504 X |
| 3,463,663 | 8/1969 | Chopra ................................ | 427/250 |
| 3,661,660 | 5/1972 | Wessells et al. .................... | 134/1 |
| 3,804,059 | 4/1974 | Streel ................................... | 118/726 |
| 3,978,006 | 8/1976 | Topp et al. ......................... | 204/195 S |
| 4,135,012 | 1/1979 | Su ......................................... | 427/309 |

OTHER PUBLICATIONS

Powell et al., *Vapor Deposition*, John Wiley and Sons, New York, N.Y., ©1966, pp. 606–609, 222, 225.

*Primary Examiner*—Norman Morgenstern
*Assistant Examiner*—Richard Bueker
*Attorney, Agent, or Firm*—Robert J. Wallace

[57] ABSTRACT

A method of evaporating an adherent metal electrode coating onto a surface of the zirconia exhaust gas oxygen sensor body. The zirconia is heated to an elevated temperature and the electrode metal evaporated onto the zirconia surface from an adjacent helix. The helix conforms to the zirconia surface and has electrode metal distributed throughout its length. After deposition at a rate of about 0.5–1.0 micrometers per minute is terminated, the zirconia is maintained at the elevated temperature for a few minutes and then slowly cooled for exposure to ambient conditions. Evaporation is from a conforming, closely spaced helix that also preheats the sensor body.

6 Claims, 6 Drawing Figures

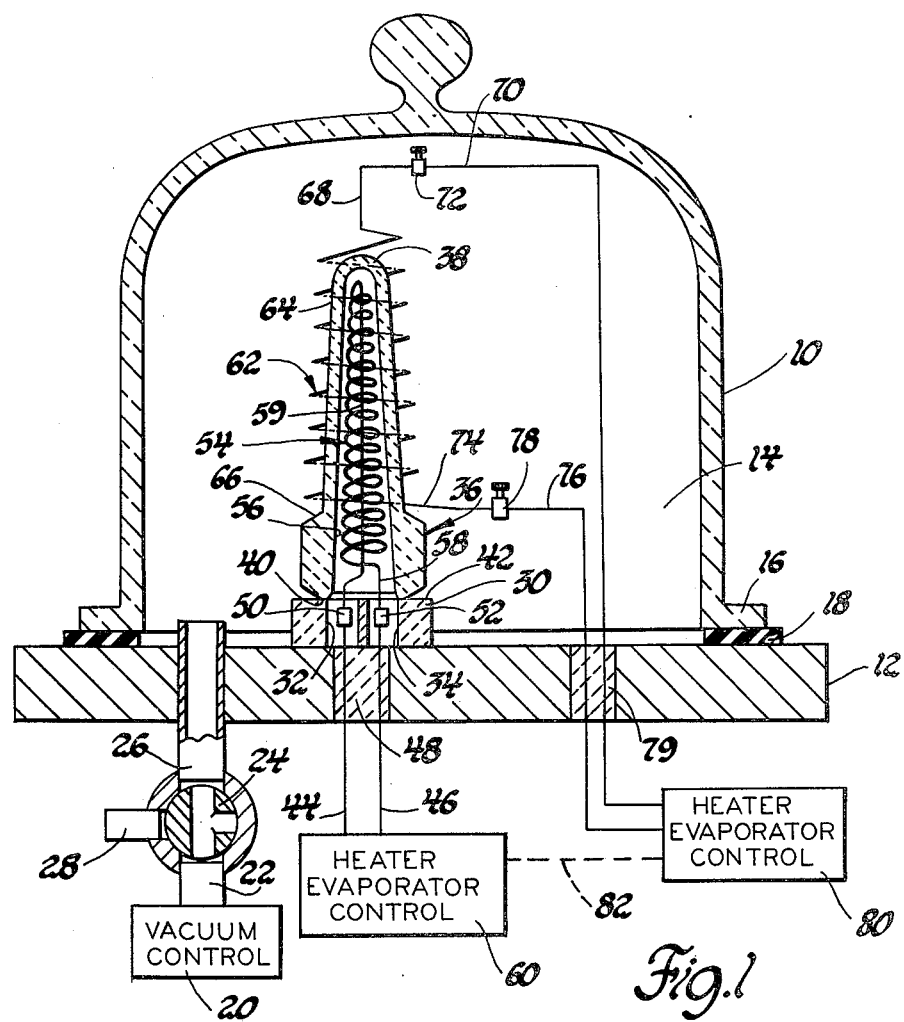

EVAPORATED ELECTRODES FOR ZIRCONIA EXHAUST GAS OXYGEN SENSORS

FIELD OF THE INVENTION

This invention relates to the electroding of zirconia exhaust gas sensor bodies. It more particularly relates to an evaporated process for depositing an adherent porous catalytic electrode on a zirconia exhaust gas oxygen sensor body.

BACKGROUND OF THE INVENTION

It is recognized that film electrodes on zirconia type exhaust gas sensor bodies should be porous and adherent. U.S. Pat. No. 3,978,006, Topp et al, discloses that catalytically active film electrodes can be applied by a variety of thin layer techniques, such as thermal vaporization, cathode atomization, gas phase deposition, chemical reduction, galvanic deposition, and by applying a platinum suspension with a brush. It also discloses heat treating such electrodes to make them porous after deposition.

My concurrently filed U.S. patent application Ser. No. 177,561, entitled "Surface Etching Before Electroding Zirconia Exhaust Gas Oxygen Sensors", which is also assigned to the assignee of this invention, describes a zirconia pretreatment process that enhances porosity and adherence of deposited electrodes. Unlike sputtered electrodes, evaporated electrodes do not have an appreciable porosity as deposited. Accordingly, it is highly desirable to pretreat the zirconia surface if the electrodes are to be produced by evaporation or the like.

In this invention I found an apparatus and method for providing highly porous adherent electrodes as deposited. In addition, the electrode metal is extremely uniformly distributed over the zirconia surface regardless as to the contour of the zirconia surface, which enhances obtaining more consistent electrode properties among groups of sensors.

OBJECTS AND SUMMARY OF THE INVENTION

An object of this invention is to provide an improved evaporation apparatus for electroding zirconia exhaust gas oxygen sensors.

Another object of this invention is to provide an improved process for evaporating catalytic electrodes onto the surface of a zirconia exhaust gas oxygen sensor body.

These and other objects of the invention are obtained in a process wherein a zirconia body is placed within a vacuum chamber adjacent a conforming resistance heating coil. The heating coil is a helix spiral generally uniformly spaced less than about 4 millimeters away from the zirconia surface and has comparatively closely spaced coil turns. A catalytic electrode metal is disposed along substantially the entire length of the coil turns. The vacuum chamber is evaporated, and the zirconia body heated by the coil to a temperature above 600° C. The heating coil current is then increased to heat at above the boiling point temperature of the catalytic metal. The current is adjusted to produce a deposition rate on the hot zirconia of at least about 60 angstroms per second on the adjacent surface of the zirconia body. After about 0.4–1.2 micrometers of the catalytic metal is so deposited, heating current through the coil is reduced enough to stop any significant further catalytic metal evaporation but not enough to allow the zirconia body to cool below about 600° C. After several minutes, coil heating current is terminated completely, and the zirconia body allowed to cool. The vacuum chamber is then brought back to atmospheric pressure and the zirconia body removed.

BRIEF DESCRIPTION OF THE DRAWING

Other objects, features and advantages of this invention will become more apparent from the following description of preferred embodiments thereof and from the drawing, in which:

FIG. 1 schematically shows a sectional view of an evaporation apparatus made in accordance with this invention;

FIGS. 2–5 show sectional views of various alternate wire strand combinations that can be used for resistance heating coils in the apparatus shown in FIG. 1; and FIG. 6 shows a sectional view of a zirconia exhaust gas oxygen sensor body coated in accordance with this invention.

DESCRIPTION OF THE PREFERRED EMBODIMENTS

Before evaporating the catalytic electrode onto the zirconia surface, I prefer to first prepare that surface to receive the electrode coating. I have found a particular surface preparation technique that provides excellent results, particularly when combined with the deposition process of this subject patent application. It is described and claimed in my concurrently filed U.S. patent application Ser. No. 177,561, entitled "Surface Etching Before Electroding Zirconia Exhaust Gas Oxygen Sensors", which is concurrently filed herewith and is assigned to the assignee hereof. I have used my pretreatment process and my electroding process on a hollow tapered zirconia thimble of a shape and dimension such as is described more fully in U.S. patent application Ser. No. 080,449, now U.S. Pat. No. 4,264,647, entitled "Reference Electrode Printing Process and Mask for Exhaust Gas Oxygen Sensor", which was filed by John Trevorrow on Oct. 1, 1979. It is also shown in U.S. Pat. No. 3,844,920 R. R. Burgett and B. W. Holleboom. Such a body is shown in FIGS. 1 and 6 of this patent application. It has inner and outer surfaces of complex curvature. It comprises a tapered cone about 3 cm long that has an integral flange at its open lower end 40. The flange forms a shoulder 66 on the outer diameter of the cone, which is about 0.6 cm next to the shoulder.

In the electroding pretreatment process of my aforementioned U.S. Ser. No. 080,449, (U.S. Pat. No. 4,264,647) about 6–8 of such tapered hollow zirconia thimbles are placed in a cylindrical 500 ml polytetrafluoroethylene beaker on top of a horizontal polytetrafluoroethylene support spaced about 1–2 centimeter above the bottom of the beaker. The beaker contains about 250 ml of an acid mixture consisting essentially of about 20–35% by volume concentrated hydrofluoric acid and the balance concentrated sulfuric acid, with up to about 6% by volume water. By concentrated hydrofluoric acid, I mean one which contains about 48% by weight HF. By concentrated sulfuric acid, I mean one that contains 98% by weight $H_2SO_4$. The quantity of the acid mixture is sufficient to cover all of the zirconia thimbles by more than about 1 centimeter. The acid mixture is maintained at about 180°–260° C. and the thimbles are continuously immersed in it at that temperature for about 0.5–4.0 hours. It is preferably continuously stirred during this time, as for example by magnetic stirring. For the magnetic stirring, a polytetrafluoroethylene encapsulated iron rod is disposed in the beaker beneath the thimble support. The beaker can be placed on a hot plate that also has means for magnetically rotating the iron rod in the beaker. Heat from the hot plate is adjusted to maintain the etchant temperature in the beaker at about 180°–260° C. during etching and magnetic stirring adjusted to be about 1–5 revolutions per second. As etching proceeds, the etchant may gradually increase in viscosity to such an extent that magnetic stirring is impeded. If so, a fresh 50 ml quantity of the acid can be preheated and added to the beaker to thin the etchant. This may occur after only about 1–2 hours. If so, I prefer to continue etching for another 1–2 hours after adding the fresh acid quantity, for a total of 2–4 hours.

Then the beaker is transferred to a 100° C. water bath on an ultrasonic agitation apparatus, and the etchant agitated ultrasonically for about one hour. In the alternative I believe it would be preferable to ultrasonically agitate the etchant during the aforementioned 0.5–4.0 hour etching period at 180°–260° C., perhaps continuously and at least during its later portions. However, no equipment was available to me to confirm this. Accordingly, I was required to perform the ultrasonic agitation in a separate following step. I would prefer to do it along with the magnetic stirring. I expect that only about 0.5 hour of ultrasonic agitation is all that is needed and that 1.0 hour merely insures consistent satisfactory results. More than 1.0 hour does not seem objectionable, just unnecessary.

In any event, after the ultrasonic agitation is completed, the zirconia thimbles can be removed from the beaker. They are then rinsed in deionized water, rinsed in acetone, rinsed again in deionized water, and then dried.

The zirconia thimbles are then fired in an oxidizing environment such as air for about 1 hour at a temperature of 1000° C., using a programmed fire in which the zirconia bodies are heated over a period of at least 2 hours from room temperature to 1000° C. and cooled at least that slowly. After the zirconia bodies have cooled sufficiently to permit them to be handled, they are ready for deposition of the electrode material by evaporation in accordance with this invention. The aforementioned 1000° C. fire temperature can be at any temperature of about 800°–1250° C., with appropriate longer and shorter time adjustments made from one hour for deviations below and above 1000° C., respectively.

Reference is now made to the drawing, in which FIG. 1 schematically shows a vacuum evaporation apparatus for practicing this invention. The apparatus includes a glass bell jar 10 which is supported by a steel base plate 12, which together comprise a vacuum deposition chamber that is indicated by reference numeral 14. A circumferential flange 16 on the open end of the ball jar 10 is spaced from the base plate 12 by means of an annular rubber seal 18.

The vacuum deposition chamber 14 is evacuated by means of a vacuum control 20 acting on the vacuum deposition chamber 14 through lower tube 22, valve 24 and upper tube 26. When valve 24 is appropriately positioned, the vacuum deposition chamber 14 directly communicates with the vacuum control. When the valve 24 is rotated 90° counterclockwise, it communicates vacuum deposition chamber 14 with ambient pressure through horizontal pipe 28, valve 24, and upper pipe 26. The vacuum control 20 can be any of the normal and accepted types of evacuation and monitoring systems ordinarily used in vacuum evaporation apparatus. It forms no part of this invention.

Resting on base plate 12 within vacuum deposition chamber 14 is an alumina support pedestal 30 having two holes 32 and 34 therein. A tapered hollow zirconia thimble 36 is supported on the alumina pedestal 30. The zirconia thimble 36 has a closed upper end 38 which is of smaller diameter than its open lower end 40. The thimble 36 is vertically oriented with its open end 40 resting on, and supported by, the upper surface 42 of alumina pedestal 30.

Two terminal leads 44 and 46 extend through a glass feed-through 48 in base plate 12 into the holes 32 and 34, respectively, of the alumina pedestal 30. Terminals 44 and 46 respectively intersect with connectors 50 and 52, which are shown within holes 32 and 34. However, they need not necessarily be located here. They are only shown here for convenience of illustration. As a practical matter, it may be desirable to route them horizontally through other holes (not shown) in the pedestal to permit easier connection. In any event, extending up from connectors 50 and 52 is a helical resistance heating coil 54 formed of intertwined, i.e. twisted, single strands of tungsten wire and platinum wire. A cross-sectional view of the twisted single strands is shown in FIG. 2. The tungsten wire has a diameter of 0.5 millimeter. The platinum wire has a diameter of 0.25 millimeter.

The heater coil 54 is a tapered helix that generally conforms to the taper on the inner surface 56 of zirconia thimble 36. It is spaced about 3 millimeters away from the inner surface 56 and extends along substantially the entire length of inner surface 56, up to and including the upper end 38. Heater coil 54 has 15 or 16 closely spaced turns which are spaced less than about 2 millimeters apart. The lower end 58 of heater coil 54 is in low resistance communication with terminal lead 46 through connector 52. The upper end of the heater coil 54 has an extension 59 that passes axially along the center of the helix down to the open lower end 40 of the thimble where it is in low resistance electrical communication with terminal lead 44 by means of connector 50. Terminal leads 44 and 46 are in turn connected to a heater evaporator control unit 60 which is a means for passing electrical current through the coil 54, depending upon whether one is merely heating the thimble 36 or attempting to evaporate platinum off of the coil onto the inner surface 56 of the thimble 36.

A second coil 62 surrounds the outer surface 64 of thimble 36 above thimble shoulder 66. Coil 62 extends all the way from shoulder 66 to the top 38 of the thimble. It is spaced about 4 millimeters away from the outer surface 64 of thimble 36 and has a number of closely spaced turns, in this example about 8, which are uniformly spaced about 4 millimeters or less apart. Coil 62 is similar to coil 54 in that it is formed of intertwined, i.e. twisted, single strands of tungsten wire and platinum wire. The upper end 68 of outer coil 62 is affixed to a terminal lead 70 by means of an upper connector 72. The lower end 74 of outer coil 62 is affixed to another terminal lead 76 by means of a lower connector 78. Connectors 72 and 78 can be of the thumb screw type. Such connectors can also be used for the connectors 50 and 52 on the inner coil 54. The outer coil terminal leads 70 and 76 pass through a glass feed through 79 to a second heater evaporator control unit 80.

Heater evaporator control unit 80 and heater evaporator control unit 60 can be similar units that similarly control their respective heating coils 54 and 62. In addition, when one desires to simultaneously coat the inner surface 56 and the outer surface 64 of thimble 36, one would like to have these heater evaporator control units 60 and 80 interconnected to coordinate their action. This coordinated action is indicated by the dotted line 82. The specific nature of these heater evaporator control units 60 and 80 form no part of this invention and can be of any suitable type. It is presumed that they would include a power supply and a variable resistance. They may also include means (not shown) to monitor thimble temperature during heating and evaporation. On the other hand, it may be desirable to simply calibrate the heater evaporator control unit beforehand to ascertain appropriate power settings which produce the desired temperature in the zirconia thimble 36 and the heating coils 54 and 62.

In the foregoing description, I mention that each of coils 54 and 62 are formed of twisted single strands of 0.5 mm tungsten wire and 0.25 mm platinum wire, and that FIG. 2 shows a cross-sectional view of the twisted strands. In FIG. 2, the tungsten wire is designated by reference numeral 84 and the platinum wire is designated by reference numeral 86. However, if higher temperature heating or faster evaporation is desired, particularly with zirconia bodies of higher mass, it may be desirable to incorporate additional strands of tungsten wire, as can be seen in FIGS. 3, 4 and 5. FIG. 3 shows a cross-sectional view of a heater coil comprising two strands 84a and 84b of tungsten wire twisted together with a single strand 86 of platinum wire. Analogously, FIG. 4 shows four strands 84a, 84b, 84c and 84d of tungsten wire twisted together with a single strand of platinum wire 86.

Also, the coils 54 and 62 need not be made of single strands of the catalytic metal. For example as shown in FIG. 5, four strands of tungsten wire 84a, 84b, 84c and 84d are twisted together with two strands 88 and 90 of palladium wire having a diameter of about 0.15 millimeter. If the metal to be evaporated is in a wire form that is especially small, as is the case with palladium, one may choose to use two strands to enhance the rate of evaporation from the coil. The precise number and diameter of the strands used, the number of strands of wire used, the exact spacing and the like, can be varied. The particular examples of wire diameters, numbers of strands of tungsten wire, the spacing of the turns and the like, can also be varied depending on the size and shape of the zirconia surface that is being coated. In any event, the important consideration is that there be a fairly close spacing of the turns and a close spacing of the coil to the surface being coated, so that a uniform coating is applied to the zirconia surface. It should also be noted that if alloys of two catalytic metals, such as palladium or platinum, are desired for an electrode coating, then wires of both metals would be included in the coil. Still further, it is convenient to include the catalytic metal in the coil as a wire. However, it is also contemplated that a coating of the catalytic metal on the tungsten wire could be used instead of or in combination with a wire of the catalytic metal twisted with the tungsten wire.

To use my electroding process in the foregoing apparatus, one of the zirconia thimbles 36 pretreated as hereinbefore described is placed on zirconia pedestal 30 over coil 54. Coil 62 is placed over it. Bell jar 10 is then seated on seal 18 to form vacuum deposition chamber 14. Valve 24 is then rotated to communicate vacuum deposition chamber 14 with the vacuum control 20. After the vacuum chamber is pumped down to a pressure of about $2 \times 10^{-5}$ Pa, both of the heater evaporator controls 60 and 80 are turned on to a previously calibrated setting which will pass sufficient electrical current through their respective coils 54 and 62 to heat the zirconia thimble to above about 600° C. but not evaporate the platinum wire 86. After the zirconia has been heated to about 600°–800° C. for approximately 5 to 15 minutes, platinum evaporation is started. Apparently, a minimum of 3 minutes preheat at 600°–800° C. is required. Five minutes generally provides adequate results. On the other hand, preheating for periods longer than 15 minutes do not appear to provide any added benefits but are not objectionable. For platinum and palladium, preheating above about 600° C. seems necessary to get good adhesion. Preheating above about 800° C. is to be avoided because the power setting on heating coils 54 and 62 has to be set so high that platinum evaporation can occur. After a deposition of about 1–2 minutes, to provide a minimum electrode film thickness of about 0.4–1.2 micrometers, evaporation is terminated. The precise coating thickness forms no significant part of this invention except to the extent that if coating thicknesses appreciably in excess of 1.2 micrometers are used the coating tends to be less porous and slower in response to changes in exhaust gas composition. In general, film thicknesses less than about 0.4 micrometer appear to provide higher resistance coatings, presumably due to lack of continuity in the film.

Evaporation is terminated by returning the heater evaporator controls 60 and 80 to the initial power setting which heats the zirconia thimble 36 without evaporating the platinum 86 from the coils 54 and 62. This return to the initial power setting is maintained for at least 3 minutes, and preferably 5 to 10 minutes before cooling to room temperature. In essence, I prefer to maintain the thimble 36 at a temperature in excess of about 600° C. after evaporation for at least about 3 minutes to insure that there is both a chem-absorption and phys-absorption of the resultant platinum coatings 92 and 94 on surfaces 56 and 64.

The resultant coated thimble is cooled from above 600° C. to below 200° C. without quenching. Moderate to slow cooling is what I have in mind, as for example progressively stepping down the heater evaporator controls to allow the thimble 36 to cool from 600° C. to below 200° C. in 2 hours or more. This is done to avoid any weakening of the platinum-zirconia bond due to rapid cooling.

After the thimble 36 has been cooled to below 200° C., and preferably even to room temperature, vacuum deposition chamber 14 is returned to the ambient, i.e. atmospheric, pressure by rotating valve 24 to allow ambient air to enter vacuum chamber 14 through pipes 28 and 26. The bell jar 10 can then be raised up from plate 12 and the cooperating sealing 18, and the coated zirconia thimble 36 removed. The coated thimble is shown in FIG. 6. It can be covered with a protective porous coating, if desired, and is ready for assembly in an oxygen sensor unit such as shown in the aforementioned U.S. Pat. No. 3,844,920, R. R. Burgett and B. W. Holleboom.

The embodiments of the invention in which an exclusive property or privilege is claimed are defined as follows:

1. In a method of evaporating an adherent metal electrode onto a surface of a zirconia exhaust gas oxygen sensor body, the improvement of heating the zirconia to above about 600° C. before evaporation commences, evaporating electrode metal onto the zirconia surface from a conforming resistance heating helix having the electrode metal distributed substantially throughout its length, the helix being spaced less than about 4 mm from the zirconia surface, evaporating the metal onto the zirconia surface from the conforming resistance heating helix at a rate of about 0.5–1.0 micrometers per minute, and maintaining the zirconia body above about 600° C. for at least 3 minutes after terminating evaporation and before exposing the evaporated metal to atmospheric pressure.

2. In a method of evaporating a catalytic electrode coating onto a surface of a zirconia exhaust gas oxygen sensor body, the improvement of placing the zirconia body in a vacuum chamber adjacent a heating coil containing a catalytic electrode metal, the heating coil has a contour generally corresponding to the zirconia surface to be coated and is generally uniformly spaced less than about 4 mm away from the surface, evacuating the chamber and heating the zirconia body for a few minutes to a temperature above about 600° C., evaporating catalytic metal from the heating coil onto the thus heated zirconia at a deposition rate of the order of 100 angstroms per second, heating the zirconia for a few minutes after said catalytic metal deposition to enhance chem-absorption and phys-absorption of the resultant metal coating on said surface, cooling the zirconia to below about 300° C., and then bringing the vacuum chamber back to atmospheric pressure.

3. In a method of evaporating at least one metal selected from the group consisting of platinum and palladium onto a zirconia exhaust gas oxygen sensor body surface to form an electrode, the improvement wherein the zirconia is at a temperature of about 600°–800° C. when evaporation commences, the metal is evaporated from a resistance heating helix having the metal distributed substantially throughout its length and a contour corresponding to that of the zirconia surface and the resistance heating helix is spaced less than about 4 mm from the zirconia surface, the zirconia surface is heated to a temperature above about 600° C. by the helix for at least 5 minutes before evaporation of said metal commences, said metal is evaporated onto the zirconia surface to a thickness of about 0.4–1.2 micrometers in about 1–2 minutes, the zirconia surface is maintained above about 600° C. for a few minutes after evaporation is discontinued, and the zirconia surface is slowly cooled to below about 200° C. before exposing it to room temperature conditions, effective to provide an electrode that is generally uniform in thickness, quickly responsive to oxygen content changes in a gas mixture, and adherent to the zirconia surface.

4. In a method of evaporating at least one metal selected from the group consisting of platinum or palladium onto a surface of a zirconia exhaust gas oxygen sensor hollow tapered thimble to form a platinum electrode thereon, the improvement of placing the zirconia thimble in a vacuum deposition chamber adjacent a resistance heating helix having a contour conforming to that of the zirconia surface to be coated and having a wire of said metal disposed along its length, spacing the resistance heating helix less than about 4 mm from the zirconia surface and providing helix turns spaced less than about 4 mm apart, passing electrical current through the helix to heat the thimble to a temperature of about 600°–800° C. for at least about 5 minutes after chamber evaluation and before metal evaporation, increasing electrical current through the helix until platinum evaporates therefrom and deposits onto the adjacent hot zirconia surface at a rate of about 60–100 angstroms per second, decreasing the electrical current through said resistance heating helix after a desired metal thickness is deposited on said zirconia only sufficiently to discontinue said metal evaporation but sufficient to maintain said zirconia surface above about 600° C. for at least 5 minutes after evaporation stops, allowing the zirconia surface to cool over a period of at least 2 hours, and then releasing the vacuum on the chamber.

5. A method of forming an adherent and porous metal electrode onto a surface of a zirconia exhaust gas oxygen sensor body, the improvement comprising etching the zirconia surface with an acid mixture consisting essentially of about 20–35% by volume concentrated hydrofluoric acid and the balance concentrated sulfuric acid for at least about 0.5 hour at about 180°–220° C., ultrasonically agitating the etchant for at least about an hour during etching, then heating the zirconia body to about 800°–1250° C. for at least about an hour, heating the zirconia body to about 600°–800° C. for several minutes in an evacuated chamber, evaporating electrode metal onto the hot zirconia surface from a conforming resistance heating helix having the electrode metal distributed substantially throughout its length, the helix being spaced less than about 4 mm from the zirconia surface, evaporating the metal onto the zirconia surface from the conforming resistance heating helix at a rate of about 0.5–1.0 micrometers per minute, and then maintaining the zirconia body above about 600° C. for at least 3 minutes after terminating evaporation and before exposing the evaporated metal to atmospheric pressure.

6. An apparatus for evaporating a catalytic metal electrode onto inner and outer surfaces of a hollow tapered zirconia exhaust gas oxygen sensor thimble comprising a vacuum deposition chamber and associated evacuation means, a support in the chamber for the thimble, inner and outer resistance heating coils conforming to said inner and outer surfaces respectively, said coils each being of intertwined strands of tungsten and catalytic metal, and means for regulating electrical current passing through the coils to successively preheat the zirconia thimble, evaporate the catalytic metal onto the zirconia thimble and post-heat the zirconia thimble.

* * * * *